United States Patent [19]

Snorrason

[11] Patent Number: 5,336,675

[45] Date of Patent: Aug. 9, 1994

[54] METHOD OF TREATING MANIA IN HUMANS

[76] Inventor: Ernir Snorrason, Stigahlid 80, IS-105 Reykjavik, Iceland

[21] Appl. No.: 842,322

[22] Filed: Feb. 28, 1992

[30] Foreign Application Priority Data

May 14, 1991 [IS] Iceland ................................. 3706
Jul. 31, 1991 [IS] Iceland ................................. 3706
Feb. 13, 1992 [DK] Denmark .......................... 183/92

[51] Int. Cl.$^5$ .............................................. A61K 31/55
[52] U.S. Cl. ................................................. 514/215
[58] Field of Search ..................................... 514/215

[56] References Cited

FOREIGN PATENT DOCUMENTS

| | | |
|---|---|---|
| 0311303 | 4/1989 | European Pat. Off. . |
| 0326106 | 8/1989 | European Pat. Off. . |
| 0383318 | 8/1990 | European Pat. Off. . |
| 0412822 | 2/1991 | European Pat. Off. . |
| 0413667 | 2/1991 | European Pat. Off. . |

OTHER PUBLICATIONS

Gilman, et al., Goodman and Gillman's, The Pharmacological Basis of Therapeutics, pp. 150–158 and 238–241 (1990).
Bretagne and Valetta, Anesth. Analges. 22, pp. 285–292 (1965).
Thomsen & Kewitz, "Pharmacological Interventions on Central Cholinergic Mechanisms in Senile Dementia", (1989).
Vander et al., "Human Physiology", pp. 184–185 (1985).
"Martindale," pp. 1118–1119 (1992).
Heller-Brown, "Atropine, Scopolamine, and Related Antimuscarinic Drugs", 8:150–158 (1989).
Bech P. et al., Mania Scale (MAS), Scoring instructions and glossary of definitions, 1986, Acta. Psych. Scan. suppl., pp. 29–31.
Risch et al., Differential Mood Effects of Arecoline in Depressed Patients and Normal Volunteers, 1983, Psychopharmacology Bulletin, vol. 19, No. 4, pp. 696–698.

Davis K. L. et al., Physostigmine in Mania, 1978, Arch Gen Psychiatry, vol. 35, pp. 119–122.
Janowsky D. S. et al., Role of Acetylcholine Mechanisms in the Affective Disorders, 1987, Psychopharmacology: The Third Generation of Progress, ed. Herbert Y. Meltzer, Raven Press, New York, pp. 527–533.
Janowsky D. S. et al., Cholinomimetic and Anticholinergic Drugs Used to Investigate an Acetylcholine Hypothesis of Affective Disorders and Stress, 1984, Drug Development Research, vol. 4, pp. 125–142.
Fritze, J. et al., Erythrocyte Acetylcholinesterase in Psychiatric Disorders and Controls, 1987, Biol Psychiatry, vol. 22, pp. 1097–1106.
Proskurnina et al., J. Gen. Chem. 22, 1988–1902, Chemical Abstract, 47, 6959, (1953).
Paskow, "New Neuromuscular Blocking Agents", Hdbk, Exp. Pharmac. y, 653–672, (1986), p. 4.
Bretagne and Valletta, Anesth. Analges. 22, 285–292, (1965), p. 4.
Wislicki, Brit. J. Anaesth. 39, 963, (1967), referred to at p. 4, line 26.
Cozanitis et al, Der Anaesthesist, 416–421, (1971), referred to at p. 4, line 27.
Thomsen and Kewitz, Life Sciences, 46, 1553–1558, (1990), referred to at p. 4, line 30.
Thomsen and Kewitz, Dementia, 1990, 46–51.
Welner, et al., Extract from Psykiatri (1985) p. 1.
"Martindale," pp. 1332–1335 (1992).
Janowsky et al, Lancet, 2, pp. 632–635 (1972).
Merck Index, 11th ed., 1989, #4245.

*Primary Examiner*—Marianne M. Cintins
*Assistant Examiner*—Kimberly R. Jordan
*Attorney, Agent, or Firm*—Foley & Lardner

[57] ABSTRACT

Mania is treated by administering, to a patient in need thereof, galanthamine or a salt or derivative thereof or a functional equivalent of galanthamine, the functional equivalent being an acetylcholinesterase inhibitor which is active substantially selectively at nicotinic receptor sites.

18 Claims, 2 Drawing Sheets

METHOD OF TREATING MANIA IN HUMANS

Mania is a severe affective disorder which almost disables the patient in the manic phases and which in most patients recure with individual intervals.

The medication used in practice until now in the treatment of affective disorders is, with respect to depression, to augment the noradrenergic and/or serotonergic activity in the brain. With respect to mania, the rationale behind the medication used in practice until now seems rather to be directed against the symptomatic relief of the psychotic behaviour of the manic patient in general, rather than against the supposed mechanism of the disease.

Thus, mania is presently treated with, e.g. lithium salts and/or in certain cases benzodiazepines or neuroleptics. Lithium is mostly used in the prophylaxis of mania but in some cases is also used in the acute treatment of mania. The treatment with lithium salts has as the advantage that it prevent the outbreaks of the manic phases. However, lithium salts have a very slow onset of action, because they pass the blood-brain barrier only very slowly (2-4 days; Welner, Joseph et al., Psykiatri, 2nd edition, F.A.D.L., Copenhagen, 1985 (textbook)) and is therefore of limited use in the acute phases. Also, lithium salts have long term side effects, such as nephrotoxicity. Furthermore, the lithium concentration in plasma has to be monitored closely to avoid intoxication: lithium is excreted through the kidneys, and just a small deviation from the normal lithium clearance increases the risk of intoxication; such small deviations can occur in connection with slimming diets, in combination with medication with diuretics, and in connection with administration of NSAID and ACE inhibitors. Also, many patients feel that they are slowed down more than wanted both motoric and psychic and it could be due to a mental side effect of lithium. Benzodiazepines such as rivotril are not used prophylactically, and do not alleviate the basic condition, but only give a symptomatic damping of some of the symptoms in mania, such as the motor and verbal activity and the voice and noise level.

Neuroleptics such as haloperidol preparations are also used in the treatment of the acute phases of mania but some people are hypersensitive to neuroleptics and reveal extrapyrimidal side effects such as symptoms like in Parkinson's disease.

Janowsky D. S., El-Yousef M. K., Davis J. M., et al. A Cholinergic adrenergic hypothesis of mania and depression. Lancet 1972:2:6732-6735, proposed an adrenergic-cholinergic balance hypothesis of affective disorders, depression being a disease of cholinergic predominance, and mania being a disease of cholinergic deficiency. Janowsky et al. found that physostigmine, a centrally active cholinesterase inhibitor, rapidly converted mania to a syndrome consistent with a psychomotor retardation. Having received physostigmine, manics became significantly less talkative, euphoric, active, cheerful, happy, friendly or grandiose and showed a decrease in flight of ideas. Patients also reported that they felt drained, being without energy, becoming apathetic and having no thoughts, Also, physostigmine has been found to cause a depressed mood in a group of euthymic bipolar patients maintained on lithium. Risch S. C. et al. (1983): Psychopharmacol. Bull, 19:696-698, have shown that some normals become depressed after receiving physostigmine.

EP 311 303 discloses novel 4-aminopyridine derivatives which are stated to be acetylcholinesterase inhibitors and are stated to be active against Alzheimer's disease. It is also stated that the derivatives exhibit antidepressant activities.

EP 413 667 discloses halogenalkylphenylalcohols, -ketones and their hydrates and states that these compounds show selective central acetylcholinesterase inhibiting effect on homogenized rat brain tissue, and that, in such experiment, enzyme from various brain regions are significantly inhibited, whereas enzyme from peripheral organs is affected only to a small degree, and that one of the compounds, in this experiment, has a strong inhibiting effect on Cortex, Hippocampus, Striatum, and Pons/medulla, whereas enzyme from the heart is not affected. It is stated that the compounds are useful as selective acetylcholinesterase inhibitors, e.g. for treatment of Alzheimer's disease, Huntingtons chorea, tardive Dyskinesia, Hyperkinesia, mania, acute panic reactions, Down's syndrome, Myasthenia gravis, Friedrich's ataxia, and pain.

EP 383 318 discloses novel aralkylamine compounds and discloses that a number of the compounds show acetylcholinesterase inhibitor activity in homogenated cerebral cortex from Wistar rats. It is stated that the compounds are indicated for senile demantia, Alzheimer's disease, Huntington's chorea, hyperkinesia and mania.

EP 412 822 discloses novel 4,4-disubstituted piperidine derivatives which have central nervous system activity as shown by inhibition of tetrabenazine-induced catalepsy, inhibition of pentylenetetrazole-induced seizure, and analgesic effect in mouse writhing tests. The compounds are stated to show an antidepressive effect which is higher than that of imipramine or nomifensine. The compounds are stated to have anticholinergic effect and are suggested for treatment of psychotic disorders, such as insomnia, mania, agitation, depression, anxiety, emesis, pains, and dementia.

According to the present invention, it has been found that mania in humans can be effectively treated by administration of galanthamine, and that galanthamine seems to not only mask the symptoms, but to provide real improvement and disappearance of symptoms faster than the usual treatment, without the severe side effects and disadvantages associated with the above-mentioned lithium, benzodiazepine and neuroleptic treatment which are the hitherto used treatments in humans.

Galanthamine is a well-known acetylcholinesterase inhibitor which is active substantially selectively at nicotinic receptor sites and has substantially no effect on muscarinic receptor sides, is capable of passing the blood-brain barrier in humans, and presents no severe side effects in therapeutically necessary dosages.

Galanthamine and acid addition salts thereof have, for many years, been known to have anticholinesterase properties.

Galanthamine, a tertiary alkaloid, has been isolated form the bulbs of the Caucasian snowdrops Galantanus woronowi (Proskurnina, N. F. and Yakoleva, A. P. 1952, Alkaloids of Galanthus woronowi. II. Isolation of a new alkaloid. (In Russian.) Zh. Obschchei Khim. (J.Gen.Chem.) 22, 1899-1902. Chem.abs. 47,6959, 1953. It has also been isolated from the common snowdrop Galanthus Nivalis (Boit, 1954).

Galanthamine has been used extensively as a curare reversal agent in anaesthetic practice in Eastern bloc countries (cf. review by Paskow, 1986) and also experimentally in the West (cf. Bretagne and Valetta, 1965: Wislicki, 1967; Conzanitis, 1971).

Pharmacokinetic studies have recently been made by Thomsen, T. and H. Kewitz. (Selective Inhibition of Human Acetylcholinesterase by Galanthamine in vitro and in vivo. Life Sciences, Vol 46, pp. 1553-1558 (1990), and, by the same authors, Galanthamine Hydrobromide in a Long-Term Treatment of Alzheimer's Disease. Dementia 1990, 1:46-51).

The findings according to the present invention seem to be in accordance with the above-mentioned 1973 findings by Janowski et al., the only prior art reference reporting treatment, in that galanthamine is an acetylcholinesterase inhibitor, such as is physostigmine, and thus counteracts cholinergic deficiency. On the other hand, physostigmine, used by Janowsky, has a profile of properties which is basically different from the profile of galanthamine. Thus, physostigmine, contrary to galanthamine, has a considerable effect at muscarinic receptor sites, and has a very fast onset of activity and a very short half life, of the order of minutes and at least less than an hour.

It is believed that the excellent and suprising effect against mania possessed by galanthamine is due to its specific profile of properties, the most important of the known ones of which can be summarized as follows:

capability to pass the blood brain barrier in humans, a high selectivity for acetylcholinesterase as opposed to butyrylcholinesterase (about 50-fold when measured by the in vitro method by Thomsen et al., see below), a sufficient elimination half life to warrant duration of an effective concentration of at least 4 hours, probably at least 6 hours, a relatively low toxicity in therapeutical concentrations, capability of being effective in doses which are sufficiently low to keep peripheral side effects low Galanthamine must be considered as being a very desirable drug for the treatment according to the invention: The elimination half life of galanthamine hydrobromide is over four hours; it shows a practically complete renal elimination; its two metabolites, epigalanthamine and galanthaminone are both probably inactive. A complete elimination of metabolites and galanthamine takes place in 72 hours. Galanthamine has been used in Eastern Block countries since around 1958 as an anticurare agent in anesthesiology, and a considerably number of patients have been treated with galanthamine without any reported case of liver toxicity or serious side effects. Galanthamine hydrobromide, being a tertiary amine and lipid soluble, is absorbed rapidly from the gut and transverses the blood brain barrier easily. The common side effects, other than the ones related to cholinergic crisis, are either nausea or vomiting, and a slight headache. However, these side effects are rare, especially when care is taken to start medication in low doses such as mentioned above.

With most patients, mania is a recurring disease, starting with hypomanic stages developing into mania, but it is difficult even within the same patient to predict the onset of a new hypomanic/manic phase or the duration thereof. This means that it is of great importance to have a drug, like galanthamine, which has an onset of action of as little as a few minutes.

Accordingly, a central aspect of the present invention relates to a method for the treatment of mania in humans, comprising administering, to a human patient in need thereof, an effective amount of galanthamine.

The galanthamine can suitably be administered orally in the form of an acid addition salt, e.g. the hydrobromide, but other administration forms are possible and realistic, such as is described below.

The effective amount will normally be referred to as a therapeutically effective amount, but the invention also comprises the cases where treatment is started before the symptoms have fully developed, e.g. prophylactically in hypomanic stages. "Prophylaxis" in the classical meaning of this term, e.g. such as lithium is administered for prophylacting mania, would normally not come into consideration because galanthamine and functional equivalents have a fast onset of action.

Because galanthamine has substantially no effect on the activity at muscarinic receptor sites, as apparent from its high selectivity for acetylcholinesterase as opposed to butyrylcholinesterase, it will not give rise to the often severe side effects on the heart which are associated with cholinesterase inhibitors which have a low selectivity for acetylcholinesterase as opposed to butyrylcholinesterase. Galanthamine has a selectivity for acetylcholinesterase opposed the effect on butyrylcholinesterase of 60 to 1.

The amount of galanthamine is preferably adjusted individually based upon observation of the effect of initially very low dosages. There is as considerable difference with respect to how sensitive individuals are to acetylcholinesterase inhibitors. Thus, the amount of galanthamine is suitably adjusted by means of a regimen starting at low dosages, e.g. 1 mg, preferably at 5 mg, per day, but, if appropriate, even as low as 0.1 mg per day, if the dosage is well tolerated by the patient within the first two hours the dosages is increased to, e.g. 10 mg per dosage dosed 3 to 4 times per day or in some severe cases to 60 mg or more per day dosed over 3 or 4 times. The increase of the dosages is suitably discontinued when the dosage of galanthamine 1) positions the affective mood of the patient in a condition of at the most hypomania, that is, a score of at the most 14 on Bech's Mania Scales described by Bech et al. Acta Scand. Psych. 1986, suppl. pp 29-31, preferably at the most 12, more preferably at the most 10, still more preferably at the most 8, and most preferably at the most 5, 2) augments the quantity and quality of the sleep in the patient (an increase in the quality of the sleep is an increase in the proportion of REM sleep), but 3) still gives substantially no heart side effects, and 4) is lower than the amount which will give rise to a cholinergic crisis.

Because cholinergic crisis, a life-threatening dose-dependant side effect of all kinds of acetylcholinesterase inhibitors, should, by all means, be avoided, it is recommended to start with the low dosages as mentioned above and furthermore not to exceed 150 mg per day and preferably not to exceed dosages above 60 mg per day, unless the patient shows a very low sensitivity to acetylcholinesterase inhibitor, in which case higher doses, such as 200 mg per day, could be used.

The effect of the galanthamine against the patient's mania is suitably measured by scoring the symptoms of the patients in accordance with the guidelines in Bech's mania Scales as described in Example 2. Referring to that scale, the patient's point score should preferably, where possible, be reduced to at the most 14, which is the limit between manic and hypomanic stages, more preferably at the most 5 which is the limit between hypomanic and normal stages.

The treatment according to the invention should preferably be continued until the manic phase is over. As a measure that the manic phase is over can be used the daily and later in the treatment weekly by scoring the patients according to Bech's mania Scale. When the patients have reached a score below 6, they are kept on galanthamine medication for about another two months to be sure that the patient is properly treated.

As far as is known, galanthamine is the only acetylcholinesterase inhibitor with the above-defined profile of properties which has been tested against mania in humans. While galanthamine has, indeed, given remarkable results, such as appears from the clinical data given in the examples, it is justified to presume that other acetylcholinesterase inhibitors which are functional equivalents to galanthamine with respect to its combination of high selectivity with respect to nicotinic receptor sites and capability of passing the blood brain barrier in humans in vivo, will also show a useful combination of effect against mania and acceptability in the clinic, although it cannot be ruled out that galanthamine, galanthamine salts and galanthamine derivatives, due to the special conformation of the gelanthamine ring system, have specific properties which are decisive for the remarkable effect on mania.

In accordance with the above, compounds which are functional equivalents of galanthamine are defined herein as compounds which
a) possess an at least 10-fold selectivity, preferably an at least 20-fold selectivity, more preferably an at least 40-fold selectivity, and most preferably an at least 50–60 fold selectivity, for acetylcholinesterase as opposed to butyrylcholinesterase, when measured by the in vitro method by Thomsen et al., see below,
b) are capable of passing the blood brain barrier in humans in vivo.

A useful drug for the treatment of mania in accordance with the present invention has a pharmaceutically acceptable, low toxicity in therapeutical concentrations, and is capable of reducing the point score, on Bech's Mania Scales (see below), to at the most 14, preferably at the most 5 in a randomly selected group of human mania patients in a double blind test, in doses which are sufficiently low to keep peripheral side effects acceptably low and to avoid cholinergic crisis.

As will be understood from the above definition, a compound can be subjected to well-defined and relatively short-lasting tests (see below) to determine whether it fulfills criterion a) above. Then, the likelihood whether the compound will pass the blood brain barrier in humans in vivo (criterion b)) can be assessed in a model. One such model is a whole rat brain model in which rats are given the acetylcholine esterase in vivo and are then killed whereupon homogenate of the rat brain is examined with respect to the acetylcholinesterase activity; the result is then compared to the acetylcholinesterase activity in rat brains not treated with acetylcholinesterase inhibitors. Another rat model could be the measurement and comparison of acetylcholinesterase activity in cerebrospinal fluid in vivo in the same rat before and after treatment. If the compound fulfills criterion a), and its likelihood of passing the blood brain barrier has been established in one of the above-described rat brain models, it will be a candidate drug. An initial determination of toxicity is necessary in cases before any effect in humans can be assessed; such initial determination of toxicity can be performed by pharmacologic tests in a manner known per se. After the pharmacological tests, the capability of the candidate drug of passing the blood brain barrier in humans in vivo can be determined by the method described below. If the candidate drug has been found to possess this capability, it can be passed to the mania testing proper. Optionally, the candidate drug can be subjected to additional short-lasting tests, such as the in vivo selectivity test described by Thomsen et al., and a test to determine whether it increases cortisol level in humans. Both of these tests give further indication of whether the candidate drug has a spectrum of properties equivalent to galanthamine with respect to what must be presumed to be essential properties. Peripheral side effects will be assessable when the effect is tested clinically, which is acceptable from an experimental and ethical point of view, provided the toxicity has first been assessed by the above-mentioned pharmacological tests. With respect to the final assessment of the candidate drug's effect on mania, it is evident that a rational and efficient design of the assessment will involve an initial test on one or a few patients and, provided the initial test is positive, the above-mentioned conclusive double blind test. Because of the well-defined and brief character of all of the tests, and especially the well-defined in vitro character of the initial screening, the test series for identifying useful functional equivalents of galanthamine is a reasonable an not burdensome routine which is within the realm of the person skilled in the art.

Functional equivalents and derivatives of galanthamine which are useful in the method of the invention will be employed in the same manner as stated herein for galanthamine. Whenever quantities of such a functional equivalent or derivative are referred to herein, the quantities are given as the equipotent quantity of galanthamine hydrobromide with respect to inhibition of acetylcholinesterase, that is, as the quantity of galanthamine hydrobromide which result in the same inhibition of acetylcholine esterase in the above-mentioned in vitro test according to Thomsen et al as does the functional derivative or derivative.

The selectivity of the acetylcholinesterase inhibitor for acetylcholinesterase as opposed to butyrylcholinesterase can be determined by in vitro and in vivo tests as described by Thomsen and Kewitz in the above mentioned paper Selective Inhibition of Human Acetylcholinesterase by Galanthamine in vitro and in vivo, Life Sciences, Vol 46, pp. 1553–1558 (1990), and T. Thomsen, H. Kewitz and O. Pleul, J. Clin. Chem. Clin. Biochem. 26 469–475 (1988). This in vivo test is the one referred to above in connection with criterion a). Thus, with reference to this determination method, a preferred acetylcholinesterase inhibitor is one which in the in vitro method described has an at least 10-fold selectivity for acetylcholinesterase as opposed to butyrylcholinesterase, such as an at least 20-fold selectivity for acetylcholinesterase as opposed to butyrylcholinesterase, e.g. an at least 40-fold selectivity for acetylcholinesterase as opposed to butyrycholinesterase. For galanthamine, these authors found a 50-fold to 60-fold selectivity for acetylcholinesterase as opposed to butyrylcholinesterase.

The capability to pass the blood brain barrier in vivo in humans can be assessed by either by a test which could be called "Auditory brain stem response" or by a test which is based on the measurement of CRH, ACTH and cortisol. The rationale behind these tests, and the way they are performed, is explained in the following:

The auditory brain stem response test is based on the observation that manio-depressive patients are hypersensitive to cholinergic influences, one manifestation hereof being hypersensitivity to auditory signals as assessed by the increase of amplitude of auditory evoked potentials in the nuclei of the auditory system in the brain stem, i.e. on the "brain side" of the blood brain barrier. This hypersensitivity manifests itself in a lower amplitude than in normal humans when the person is not treated with a cholinergic agent such as acetylcholinesterase inhibitor; and a very significantly increase of the amplitude when the person has received a cholinergic agent, provided, of course, that the cholinergic agent is able to pass the blood brain barrier and thus enter the nuclei of the auditory system in the brain stem. See also example 3.

The other test based on the measurement of CRH (corticotropic-hormone releasing hormone released from the hypothalamus in the brain, and which releases both ACTH from the adenohypophysis and cortisol from the adrenal medulla) and ACTH (corticotropic hormone, which releases cortisol from the adrenal medulla) is carried out by measuring the CRH, ACTH and cortisol concentration in the blood in healthy persons before and after medication with acetylcholinesterase. If the concentration of all three hormone are increased after medication or at least CRH and cortisol are increased it is proven that the acetylcholinesterase has effect in the central nervous system, and since it is an in vivo experiment it is further proven that the acetylcholinesterase has passed the blood brain barrier.

As mentioned above, the selectivity of the acetylcholinesterase inhibitor can, as an additional characterization, optionally be expressed with reference to the in vivo determinations performed by Thomsen and Kewitz on galanthamine and described in the above-mentioned paper Selective Inhibition of Human Acetylcholinesterase by Galanthamine in vitro and in vivo, Life Sciences, Vol 46, pp. 1553–1558 (1990). With reference to this determination, a preferred acetylcholinesterase inhibitor is one which, upon adminisration in an amount of 10 mg to a healthy adult, results in inhibition of at least 40% of the acetylcholinesterase activity in erythrocytes from the adult within about 2–5 minutes and no substantial inhibition of butyrylcholinesterase therein, such as an acetylcholinesterase inhibitor which, when administered in an amount of 10 mg to a healthy adult, results in inhibition of at least 50% of the acetylcholinesterase activity in erythrocytes from the adult within about 2–5 minutes. For galanthamine, Thomsen and Kewitz found 65% inhibition of acetylcholinesterase in the erythrocytes within 2 minutes after administration of 10 mg of galanthamine i.v. in a healthy volunteer, whereas no inhibition of butyrycholinesterase in plasma was seen. Compounds which are contemplated to be valuable functional equivalents of galanthamine and useful in the treatment according to the invention are the galanthamine derivatives having the formula I (formula I also represent galanthamine itself)

wherein $R^1$ and $R^2$ which may be the same or different each represents a hydrogen atom or an acyl group, such as a lower alkanoyl group, e.g. an acetyl group or a straight-chained or branched alkyl group, e.g. methyl, ethyl, propyl, or isopropyl; $R^3$ is a straight or branched chain alkyl, alkenyl or alkaryl group which is optionally substituted by a halogen atom or a cycloalkyl, hydroxy, alkoxy, nitro, amino, aminoalkyl, acylamino, heteroaryl, heteroaryl-alkyl, aroyl, aroylakyl or cyano group; and $R^4$ represents a hydrogen or halogen atom attached to at least one of the ring carbons of the tetracyclic skeleton, and salts thereof, such as a hydrobromide, hydrochloride, methylsulfate or methiodide.

In the compounds of formula I, alkyl moieties preferably contain 1 to 8 carbon atoms, halogen atoms are preferably fluorine, chlorine, or bromine, especially fluorine or chlorine, aryl moieties are preferably phenyl, cycloalkyl groups are preferably 3- to 7-membered rings, especially cyclopropyl or cyclobutyl, and heteroaryl moieties are preferably 5- to 8-membered rings, e.g., thienyl, furyl, pyridyl, pyrrolyl, or pyrizanyl.

Among the compounds of the formula I are those described in EP-A-236684. The compounds of formula I may be prepared according to conventional techniques, including those described in EP-A-236684.

Other compounds which are contemplated to be valuable functional equivalents useful in the method of the invention are galanthamine derivatives of the general formula II wherein the broken line represents an optionally present double bond in one or the two of the positions shown, $R_1$ and $R_2$ are each selected independently from the group consisting of hydrogen, hydroxyl, amino or alkylamino, cyano, sulfhydryl, alkoxy of 1–6 carbon atoms, alkylthic, aryloxy, arylthio, $R_5$-substituted aryloxy, $R_5$-substituted arylthio, aralkoxy, an aliphatic or aryl carbamyl group wherein the aliphatic or aryl moiety may be $R_5$ substituted or unsubstituted, aralkylthio, $R_5$-substituted aralkoxy, $R_5$-substituted aralkylthio, aryloxymethyl, $R_5$-substituted aryloxymethyl, alkanoyloxy, hydroxy-substituted alkanoyloxy, benzoyloxy, $R_5$-substituted benzoyloxy, aryloxycarbonyl and $R_5$-substituted aryloxycarbonyl, $R_1$ may also be alkyl of up to 14 carbon atoms, or hydroxymethyl, $R_2$ may also be carboxymethyl, provided that at least one of $R_1$ and $R_2$ is hydroxy, amino or alkylamino unless $R_8$ is hydroxymethyl, $R_3$ is hydrogen, straight or branched chain alkyl of 1-6 carbon atoms, cycloalkylmethyl, phenyl, $R_5$-substituted phenyl, alkylphenyl, $R_5$-substituted alkylphenyl, heterocyclyl selected from α- or β-furyl, α- or β-thienyl, thenyl, pyridyl, pyrazinyl, and pyrimidyl, alkyl-heterocyclyl or R'-substituted heterocyclyl, where R' is alkyl or alkoxy, each $R_4$ is independently selected from hydrogen, hydroxyl, sulfhydryl, alkyl, aryl, aralkyl, alkoxy, mercaptoalkyl, aryloxy, thiaryloxy, alkaryloxy, mercaptoalkaryl, nitro, amino, N-alkylamino, N-arylamino, N-alkarylamino, fluoro, chloro, bromo, iodo, and trifluoromethyl, $R_5$ is selected from the same groups as $R_4$, $R_6$ is hydrogen, halo, trifluoromethyl or alkyl of 1 to 4 carbon atoms, $R_8$ is hydrogen or hydroxymethyl, $R_9$ is hydrogen or alkyl of 1 to 6 carbon atoms, or when $R_2$ is hydroxyl, $R_9$ may be a moiety of formula I wherein $R_9$ is hydrogen and $R_2$ is a linking bond; or $R_2$ and $R_9$ may jointly form semicarbazone, X is oxygen or $NR_5$, Y is nitrogen or phosphorus, and methylenedioxy derivatives thereof with the proviso that when X is o, $R_3$ is not methyl when $R_1$ is methoxy, $R_2$ is hydroxy, and all $R_4$ are hydrogen, or a pharmaceutically acceptable acid addition salt thereof.

Examples of subclasses and specific compounds of the formula II are given in WO 88/08708, which also discloses methods for preparing the compounds II.

Galanthamine, galanthamine derivatives and galanthamine functional equivalents, when suited therefor, may be administered orally at a dosage of e.g. 5-150 mg per day, such as 10-60 mg per day, e.g. 10-50 mg, such as 10-40 mg, per day, the dosage being adapted to the patient and the patient's response. As mentioned above, the treatment should often be started with a low dosage and then increased until the suitable dosage has been established. The dosage of galanthamine functional equivalents is expressed as the equipotent amount of galanthamine hydrobromide, the reference basis being the capability of inhibiting acetylcholinesterase in the Thomsen et al. in vitro test mentioned above.

For the oral administration, galanthamine or a galanthamine salt or derivative or a functional equivalent may be formulated, for example, as an aqueous suspension or a solution in aqueous ethanol or as a solid composition such as a tablet or capsule. Suspensions or solutions for oral administration are typically of a concentration of 1-50 mg/ml, more commonly 5-40 mg/ml, for example, 10-40 mg/ml, typically 20-30 mg/ml of galanthamine. Divided doses in the range 0.1-3 mg/kg body weight per day may prove useful. Typically, one might administer a dosage of 20-100 mg per day to a patient of a body weight of 40-100 kg, although in appropriate cases such dosages may prove useful for patients having a body weight outside this range. In other cases, dosages as low as 10 mg and as high as 200 mg may be appropriate for persons in this body weight range.

Galanthamine and its acid addition salts form crystals. They are generally only sparingly soluble in water at room temperature; therefore, injectable compositions are normally in the form of an aqueous suspension. If necessary, pharmaceutically-acceptable suspension aids may be employed. Typically, such a suspension will be employed at a concentration of 0.1-30 mg/ml, more commonly 1-30 mg/ml, for example, 5-30 mg/ml, such as 10-30 mg/ml of galanthamine. As mentioned above, typical dosage rates when administering galanthamine by injection are the range 0.01-20 mg per day depending upon the patient. For example, divided doses in the range 0.5-5 mg/kg body weight per day may prove useful. Typically, one might administer a dosage of 5-50, mg per day to a patient of a body weight of 40-100 kg, although in appropriate cases such dosages may prove useful for patients having a body weight outside this range. In other cases, dosages as low as 5 mg and as high as 200 mg per day may be appropriate for persons in this body weight range.

Galanthamine and its pharmaceutically acceptable acid addition salts, and its derivatives and functional equivalents, when suited therefor, may be administered by subcutaneous, intravenous or intramuscular injection.

The parenteral dosage rate of galanthamine can also be expressed by reference to the body weight of the patient; in this case, a normal dosage rate will often be 0.1 to 4 mg/kg body weight. Depot compositions will often deliver a dosage rate of 0.01 to 5.0 mg/kg per day.

In preparing tablets or capsules, standard tablet or capsule-making techniques may be employed. If desired, a pharmaceutically acceptable carrier such as starch or lactose may be used in preparing galanthamine or galanthamine equivalent tablets. Capsules may be prepared using soft gelatine as the encapsulating agent. If desired, such capsules may be in the form of sustained release capsules wherein the main capsule contains microcapsules of galanthamine or functional equivalents thereof which release the contents over a period of several hours thereby maintaining a constant level of galanthamine or its functional equivalent in the patient's blood.

The following specific formulations may find use in the treatment of mania:

Tablets or capsules containing 0.1, 1, 2, 5, 10 and 25 mg galantahamine hydrobromide or functional equivalent to be taken four times a day, or a sustained-release preparation delivering an equivalent daily dose.

Liquid formulation for oral administration available in 5 mg/ml and 25 mg/ml concentration.

Other interesting administration forms of galanthamine and functional equivalents are suppositories, a slow-release plaster, and other depot compositions.

All of the above-mentioned administration forms are prepared in manners known per se.

Although galanthamine must be considered as having a high degree of safety, there have been certain side effects in a few of the patients treated. These have been slight nausea in about 30% of the cases (the nausea, however, disappearing after about one week of treatment), vomiting and dizziness in 5-10% of the patients (also disappearing after about one week of treatment in most cases), and more severe side effects in 4-6% of the patients. These more severe side effects must be considered acceptable in view of the effect of the drug; however, in patients who are suspected of developing arrhythmia, it should be considered to administer, e.g., atropin in combination with the treatment according to the invention.

EXAMPLE 1

Formulation of tablets containing galanthamine

| Composition of 1 tablet containing 1 mg galanthamine | |
|---|---|
| Galanthamine hydrobromide | 0.001 g |
| Calcium phosphate | 0.032 g |
| Lactose | 0.005 g |
| Wheat Starch | 0.0056 g |
| Microcrystalline Cellulose | 0.015 g |
| Talc | 0.0007 g |
| Magnesium Stearate | 0.0007 g |

| Composition of 1 tablet containing 5 mg galanthamine | |
|---|---|
| Galanthamine hydrobromide | 0.005 g |
| Calcium phosphate | 0.024 g |
| Lactose | 0.004 g |
| Wheat Starch | 0.004 g |
| Microcrystalline Cellulose | 0.04 g |
| Talc | 0.002 g |
| Magnesium Stearate | 0.001 g |

| Composition of 1 tablet containing 10 mg galanthamine | |
|---|---|
| Galanthamine hydrobromide | 0.010 g |
| Lactose | 0.040 g |
| Wheat Starch | 0.0234 g |
| Microcrystalline Cellulose | 0.0374 g |
| Talc | 0.0036 g |
| Magnesium Stearate | 0.0012 g |
| Gelatin | 0.0044 g |

Preparation

All the tablets are prepared according to routine tabletting procedures.

EXAMPLE 2

Clinical trials of the effect of galanthamine on manic patients

Methods and materials

Drug

Nivalin tablets containing 5 mg galanthamine, obtained from Waldheim Ltd., Vienna, Austria, were used in this example.

Patients 5 persons suffering from mania with a score above 5 on the Bech's Mania Scale for whom the symptoms could not be ascribed to any disease of organic origin.

Bech's Mania Scale

To evaluate the stage of mania in the patient to be treated Bech's Mania Scale was used.

All cases were evaluated before, under and after Nivalin treatment.

Bech's Mania Scale consists of 11 items:

1. Activity (motor), score from
   0 (normal activity) up to
   4 (constantly active, restlessly energetic. Even if urged the patient cannot sit still).
2. Activity (verbal), score from
   0 (normal verbal activity) up to
   4 (impossible to interrupt, dominates completely the conversation).
3. Flights of thoughts, score from
   0 (no flight of thoughts) up to
   4 (it is difficult to impossible to follow the patient's line of thoughts as the patient constantly jumps from one topic to another).
4. Voice/Noise level, score from
   0 (natural volume of voice) up to
   4 (shouting, screaming, or using other sources of noise due to hoarseness).
5. Hostility/Destructiveness, score from
   0 (no signs of impatience or hostility) up to
   4 (overt physical violence, physically destructive).
6. Mood (feeling of well-being), score from
   0 (neutral mood) up to
   4 (extremely elevated mood, quite irrelevant to situation).
7. Self-Esteem, score from
   0 (normal self-esteem) up to
   4 (grandiose ideas which cannot be corrected).
8. Contact (intrusiveness), score from
   0 (normal contact) up to
   4 (extremely dominating and manipulating without context with the setting).
9. Sleep (average of last 3 nights), score from
   0 (habitual duration of sleep) up to
   4 (no sleep).
10. Sexual interest, score from
    0 (normal sexual interest and activity) up to
    4 (completely and inadequately occupied by sexuality).
11. Work,
A: At first rating of the patient, score from
   0 (normal work activity, up to
   4 (the patient is or ought to be hospitalized and unable to participate in ward activities).
b: At weekly ratings, score from
   0 (the patient has resumed work at his/hers normal activity level, up to
   4 (the patient is still fully hospitalized and generally unable to participate in ward activities).

The criteria for mania scored in the Bech's Mania Scale are:

A total scale score of 0–5 means that the patient is not manic.

A total scale score of 6–14 means that the patient is hypomanic.

A total scale score of 15 or more means that the patient is definitely suffering from mania.

Laboratory tests

Blood samples from all patients were examined before the start of the treatment with respect to:
Haemoglobin concentration (Hgl)
White cell count (WCc)
Differentiated white cell count (DWCc)
Mean corpuscular volume (MCV)
Mean corpuscular haemoglobin concentration (MCHC)
Packed red cells volume per 100 ml blood (PCV)
Platelets
ERS
Electrolytes ($N^a+$, $K^+$, $Cl^-$, $Ca^{++}$, $Phos^{++}$)
Liver tests (bilirubin, ALT (alaninamino transaminase), AST (aspartatamino transaminase), and GOT (glutamine-oxaloacetic transaminase)
Se-glucose
Se-oreatine Thyroidstimulating hormone (TSH)
Thyroida hormones (T3 and T4)

These tests were performed before the treatment to exclude patients with mania-like symptoms caused by a disease of organic origin from the treatment with galanthamine and were also performed during the treatment in order to document any alterations of the parameters during the treatment with Nivalin.

Other measurements

Blood pressure and ECG were measured before the start of the treatment and regularly during the treatment.

Results

With respect to the blood measurements and the blood pressure and ECG, no observable changes in the results were found during the treatment.

The following case examples are demonstrative of the effects of Nivalin on manic symptoms.

Case No. 1:

HO, a 74 year old woman with a bipolar affective disorder for over 30 years. She was hospitalized from 1988 six times. For the last year she was hospitalized three times with initially depression that evolved in three months to mania. The mania was at least of degree II according to Carlson et al. 1973. She was given T. Haldol and evolved a malignant neuroleptic syndrome in the spring 1990. (with a total white cell count over $28.00 \times 10\ 9/1$, temperature over 40 C, muscle rigidity, elevated Creatine kinase.)

With the cessation of the neuroleptic drug she recovered and became euthymic for a short while and them became depressive again. Later that year, 1990, when she evolved into a manic state again the only possible medication was a benzodiazepine in high doses. She became heavily sedated without a diminution of her manic symptoms. She had to be guarded day and night and there was also the danger of this frail woman to break her leg as she became very unsteady on her feet.

Her manic symptoms lasted usually about three months and at the time of this case her mania had lasted about three weeks and was steadily increasing, at that time definitely manic with 29 points on the Bech's Mania Score. It was decided to give her T. Nivalin 5 mg initially in the morning. She tolerated well the first 5 mg and was given T. Nivalin 5 mg×2 in the afternoon. An hour after she had taken 10 mg of T. Nivalin her behaviors had markedly changed to everybody's surprise. The next day she had 14 points on the scale, i.e. slightly hypomanic.

The biggest change was in activity (motor and verbal), and flight of thoughts. Her sleep improved slightly. But what was remarked mostly was her change in concentration. She was able to look at TV and read. Also she managed an hour long game of chess, which, incidentally, she won. But she had not been able to perform a sustained activity of any sort for days. Two days later the Nivalin treatment was stopped and she practically immediately became psychotic again.

Once started on Nivalin treatment 30 mg per day she became visibly more manageable and resumed a more normal behaviour although according to the nurses slightly hypomanic. This was repeated once again with the same result. It was decided that she should continue on T. Nivalin 30 mg a day and the benzodiazepine treatment was stopped.

HO continued on T. Nivalin 5 mg×3 for three months; then the medication was stopped and she could manage her affairs at home. A month later she developed her usual depressive episode and was then hospitalized in a depressive mood.

Case No. 2:

HAS a 47 year old woman who had been hospitalized seven time since 1984. She was mostly hospitalized when she was in a manic state but could stay at her home while depressed which always preceded her mania. She had taken an overdose of lithium just prior to her stay at the hospital and was in a lithium intoxicated state with nystagmus and ataxia.

It was considered that she would not tolerate neuroleptic medication and was put on T. Nivalin 5 mg 2×3 a day. She stayed in the hospital for a month and left practically euthymic. On the Mania Scale she dropped from initially 24 to 10 points in two days. Her activity and flight of ideas normalized the most. She was also clearly more able to concentrate and sustain a commenced activity than before the medication.

Case No. 3:

SA a 33 year old woman which had been hospitalized fourteen time since 1982 with the diagnosis bipolar affective disorder. Last winter she had been hospitalized because of a heavy depression. And in the spring she left hospital slightly hypomanic and stayed that way most of the last summer. Last December she was hospitalized with state III mania or with the maximal score on the Mania Scale which is 44 points. She was considered very sensitive to neuroleptic medication and developed always very soon extrapyramidal signs that took weeks to disappear after medication.

She was consequently very hostile to the usual medication in her manic state. She was given T. Nivalin 5 mg 2×3, and the next day she was slightly hypomanic with 11 points on the Mania Scale. This was considered as a dramatic reduction in her manic symptoms, especially by her husband that knew her well, and it was decided to try to treat her at home especially that she had developed a very hostile attitude towards the hospital and its staff and to hospitalize her would have demanded a legal step to be taken, which her husband was against. She went to her home and stayed there for over a month always slightly hypomanic. She started to neglect her medication and was later hospitalized with her will. She was given a more conventional therapy and left the hospital two months later slightly hypomanic but on lithium and a weak neuroleptic.

The initial effect was without doubt no psychomotor retardation nor anergy, but a substantial alleviation of her manic symptoms.

Case No. 4:

BS a 42 year old male that had been hospitalized since 1981 over fourteen times. He had received the diagnosis bipolar affective disorder, but also schizoaffective disorder. He was constantly on some neuroleptic medication. In his last hospitalization he did develop some simile of a manic episode and was put on T. Nivalin 5 mg 2×3 or 30 mg a day. His behaviour normalized quickly and he became visibly quite euthymic. He had been rated with 17 points on the mania scale and became within normal range as mentioned. He told the nurses that he was afraid that Nivalin made him too normal and that his social assistance would therefore be withdrawn. He was somewhat reluctant to continue the medication when he left hospital.

Case No. 5:

KS six times hospitalized since 1988 because of bipolar affective disorder. From February to May 1990 he had been hospitalized because of depression. In the spring he developed a hypomanic state that lasted practically all summer 1990. He refused to be hospitalized and in November 1990 was he by police forced to be internalized then in a highly manic state and a constant embarrassment to his environment. He was given T. Haldol and T. Rivotril and developed rapidly extrapyramidal signs, a Morbus Parkinsonlike mimic and stance even with low doses of the neuroleptic and accompanied with T. Artane (benzhexol). Then the neuroleptic was totally withdrawn and he was given 30 mg of T. Nivalin a day. He maintained that T. Nivalin made him a little bit depressive and empty in the head. The manic symptoms were manageable. He told the nurses later that the energy and augmented depression disappeared later although he continued on the Nivalin treatment. And he felt that the Nivalin treatment improved his memory which he had felt were failing him.

Conclusion

The above-mentioned five cases are all chronically ill patients with advanced affective disorder. The cases show the value of the treatment of galanthamine in manic patients.

EXAMPLE 3

Auditory brain stem response

Methods

Electrical potentials caused by click-stimulation in the ears are measured with electrodes positioned outside on the head of the examined parson. In the configuration of the potentials are components from the brain stem and the brain.

Persons

A patient suffering from bipolar manio-depression in the depressive state and a healthy person, respectively.

Drug

Tablet containing 10 mg galanthamine

BRIEF DESCRIPTION OF THE FIGURES

Results are shown in FIGS. 1A, 1B, 2A and 2B and show the potentials from a depressive patient and a healthy person, both treated and untreated.

Figure 1A:
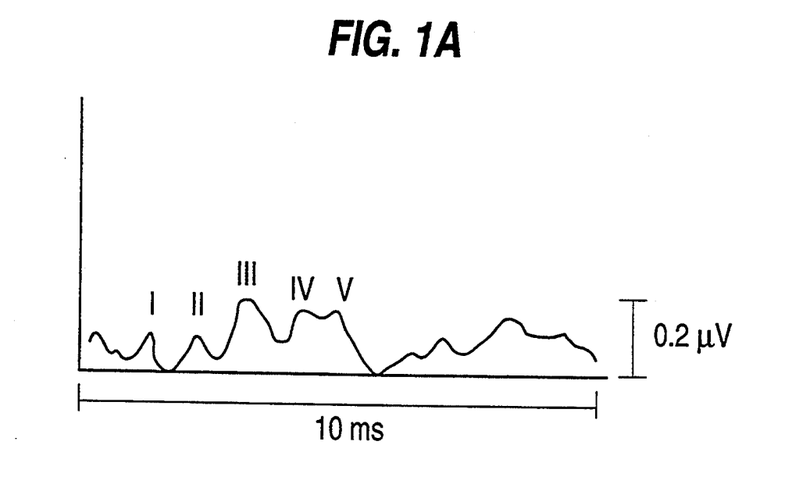
FIG. 1A shows the auditory evoked response of a depressed patient (a manio depressed patient in the depressed state) without treatment with galanthamine.
Figure 2A:
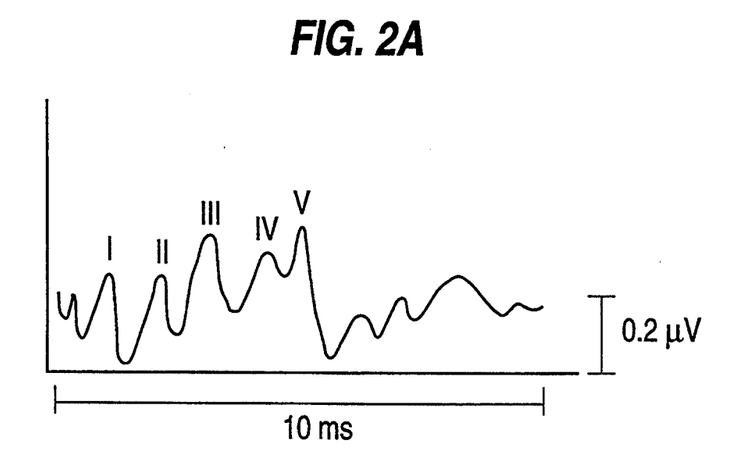
FIG. 2A shows the auditory evoked response of a healthy person without treatment with galanthamine.

FIGS. 1A, and 2A show that in the depressed patient, the auditory brain stem response without treatment has a much smaller, almost half, amplitude of the potential compared to the amplitude of the untreated healthy person.

Figure 1B:
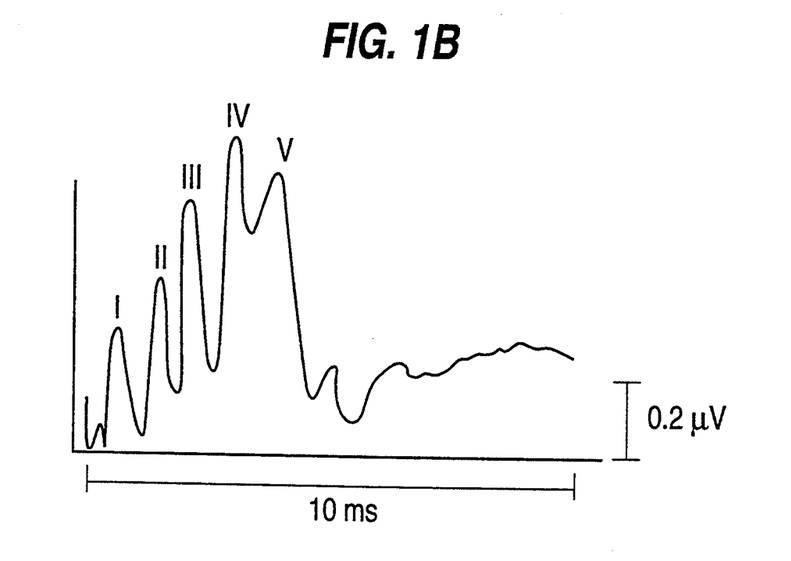
FIG. 1B shows the auditory evoked response of a depressed patient (the same as in FIG. 1A) 2 hours after treatment with 10 mg of galanthamine.

Furthermore, FIGS. 1A and 1B show a dramatically increase of the amplitude in the treated depressive patient compared to untreated persons.

Figure 2B:
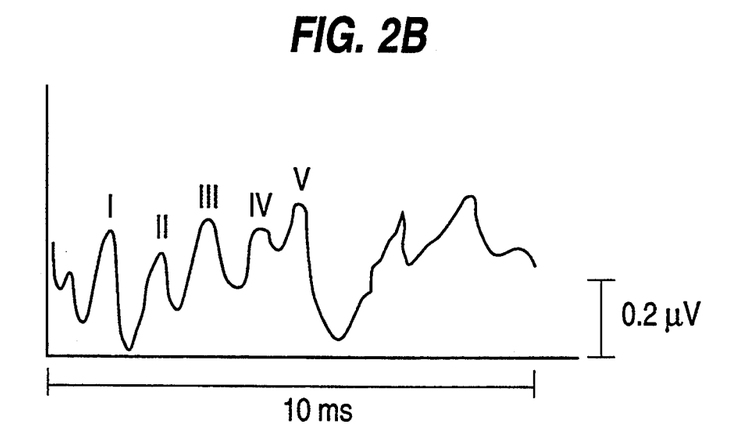
FIG. 2B shows the auditory evoked response of a healthy person (the same as in FIG. 2A) 2 hours after treatment with 10 mg of galanthamine.

Also, from FIGS. 2A and 2B it is seen that the potentials do not change from the untreated person to the treated person.

CONCLUSION.

From the results in the depressed person it is seen that the potentials change after treatment with galanthamine, such as explained above. This means that galanthamine must be able to cross the blood-brain barrier, since it is possible to inhibit in synapsis in the brain stem, which is positioned on the "brain side" of the blood-brain barrier.

LEGENDS TO FIGURES

I claim:

1. A method for the treatment of mania, comprising administering, to a human patient in need thereof, an effective amount of a pharmaceutically acceptable acetylcholinesterase inhibitor which is active selectively at nicotinic receptor sites, and which is capable of passing the blood-brain barrier in humans.

2. A method according to claim 1, in which the acetylcholinesterase inhibitor is one which has an at least 10-fold selectivity for acetylcholinesterase as opposed to butyrylcholinesterase.

3. A method according to claim 2, in which the acetylcholinesterase inhibitor is one which has an at least 20-fold selectivity for acetylcholinesterase as opposed to butyrylcholinesterase.

4. A method according to claim 2, in which the acetylcholinesterase inhibitor is one which has an at least 40-fold selectivity for acetylcholinesterase as opposed to butyrylcholinesterase.

5. A method according to claim 1, in which the acetylcholinesterase inhibitor is one which, upon administration in an amount of 10 mg to a healthy adult, results in inhibition of at least 40% of the acetylcholinesterase activity in erythrocytes from the adult.

6. A method according to claim 5, in which the acetylcholinesterase inhibitor is one which, when administered in an amount of 10 mg to an adult, results in inhibition of at least 50% of the acetylcholinesterase activity in erythrocytes from the adult.

7. A method according to claim 1, in which the cholinesterase inhibitor is one which, upon administration to a healthy human, increases the cortisol level in the human.

8. A method according to claim 1, in which the cholinesterase inhibitor is galanthamine, a galanthamine salt, or a galanthamine derivative.

9. The method of claim 1, wherein the cholinesterase inhibitor is galanthamine or a salt thereof.

10. A method according to claim 1, in which the acetylcholinesterase inhibitor is administered at a dosage of 0.1–150 mg per day, calculated as the equipotent quantity of galanthamine hydrobromide.

11. A method according to claim 10, in which the acetylcholinesterase inhibitor is administered at a dosage of 5–60 mg per day, calculated as the equipotent quantity of galanthamine hydrobromide.

12. A method according to claim 11, in which the cholinesterase inhibitor is administered at a dosage of 10–40 mg per day, calculated as the equipotent quantity of galanthamine hydrobromide.

13. A method according to claim 1 in which the amount of the acetylcholinesterase inhibitor is established by increasing the dosage from 1 mg daily until the dosage positions the patient in a condition of at the most 14 on Bech's Mania Scales and augments the quantity and quality of the patient's sleep.

14. A method according to claim 9, wherein the salt is galanthamine hydrobromide.

15. A method according to claim 9, in which the galanthamine is administered at a dosage of 0.1–150 mg per day.

16. A method according to claim 15, in which the galanthamine is administered at a dosage of 5–60 mg per day.

17. A method according to claim 16, in which the galanthamine is administered at a dosage of 10–40 mg per day.

18. A method according to claim 9, in which the amount of the galanthamine is established by increasing the dosage from 1 mg daily until the dosage positions the patient in a condition of at the most 14 on Bech's Mania Scales and augments the quantity and quality of the patient's sleep.

* * * * *

UNITED STATES PATENT AND TRADEMARK OFFICE
CERTIFICATE OF CORRECTION

PATENT NO. : 5,336,675
DATED : August 9, 1994
INVENTOR(S) : SNORRASON

It is certified that error appears in the above-identified patent and that said Letters Patent is hereby corrected as shown below:

Column 8,  lines 1-10, delete the chemical structure and replace it with:

--

--;

lines 45-55, delete the chemical structure and replace it with:

--

UNITED STATES PATENT AND TRADEMARK OFFICE
CERTIFICATE OF CORRECTION

PATENT NO. : 5,336,675
DATED : August 9, 1994
INVENTOR(S) : SNORRASON

It is certified that error appears in the above-identified patent and that said Letters Patent is hereby corrected as shown below:

line 56, after "line" insert --between carbons 3 and 4--;

line 57, delete "in one or the two of the positions shown".

Column 9,   lines 24-25, delete "formula I" and insert --formula II--.

Signed and Sealed this

Twenty-first Day of July, 1998

Attest:

BRUCE LEHMAN

Attesting Officer     Commissioner of Patents and Trademarks